(12) United States Patent
Aho et al.

(10) Patent No.: US 7,679,736 B1
(45) Date of Patent: Mar. 16, 2010

(54) SYSTEM AND METHOD FOR OPTICAL PHOTOMASK INSPECTION THROUGH PELLICLE

(75) Inventors: Marc T. Aho, Mountain View, CA (US); Thaddeus J. Wilson, Sunnyvale, CA (US); Jeff Roberts, Port Hueneme, CA (US)

(73) Assignee: n&k Technology, Inc., San Jose, CA (US)

( * ) Notice: Subject to any disclaimer, the term of this patent is extended or adjusted under 35 U.S.C. 154(b) by 0 days.

(21) Appl. No.: 12/180,522

(22) Filed: Jul. 26, 2008

Related U.S. Application Data

(60) Provisional application No. 60/952,549, filed on Jul. 27, 2007.

(51) Int. Cl.
*G01N 21/00* (2006.01)
(52) U.S. Cl. ............... 356/237.2; 356/237.1; 356/237.4; 356/237.5; 356/394
(58) Field of Classification Search ... 356/237.1–237.6, 356/394, 240.1; 250/559.01, 225, 201.2, 250/201.4; 382/145, 144, 149, 154
See application file for complete search history.

(56) References Cited

U.S. PATENT DOCUMENTS

| | | | | |
|---|---|---|---|---|
| 4,889,998 A | * | 12/1989 | Hayano et al. | 250/559.41 |
| 5,365,330 A | * | 11/1994 | Hagiwara | 356/237.3 |
| 5,436,464 A | * | 7/1995 | Hayano et al. | 250/559.01 |
| 5,539,514 A | * | 7/1996 | Shishido et al. | 356/237.4 |
| 5,563,702 A | * | 10/1996 | Emery et al. | 356/73 |
| 5,742,386 A | * | 4/1998 | Nose et al. | 356/237.2 |
| 6,834,548 B1 | | 12/2004 | Hibbs | |
| 6,835,502 B2 | | 12/2004 | Hibbs | |
| 6,836,560 B2 | * | 12/2004 | Emery | 382/145 |
| 7,060,403 B2 | | 6/2006 | Hibbs | |
| 7,133,119 B1 | * | 11/2006 | Pettibone et al. | 355/71 |

* cited by examiner

*Primary Examiner*—Sang Nguyen

(57) ABSTRACT

A pellicle correction factor is determined by comparing a first measurement of a reference photomask alone with a second measurement of that reference photomask through a reference pellicle protecting the mask layers of the photomask. A number of pellicle correction factors may be determined for different type pellicles and made accessible in pellicle correction factor lookup table of the system or supplied on a separate data storage medium. Raw Reflectance and/or Transmittance measurement data of a generic photomask through a generic pellicle is consecutively corrected for the measurement distorting effects of that pellicle by applying a matching one of the previously determined pellicle correction factors. The pellicle correction factor is preferably an attenuation signature across a predetermined measurement irradiation spectrum.

12 Claims, 6 Drawing Sheets

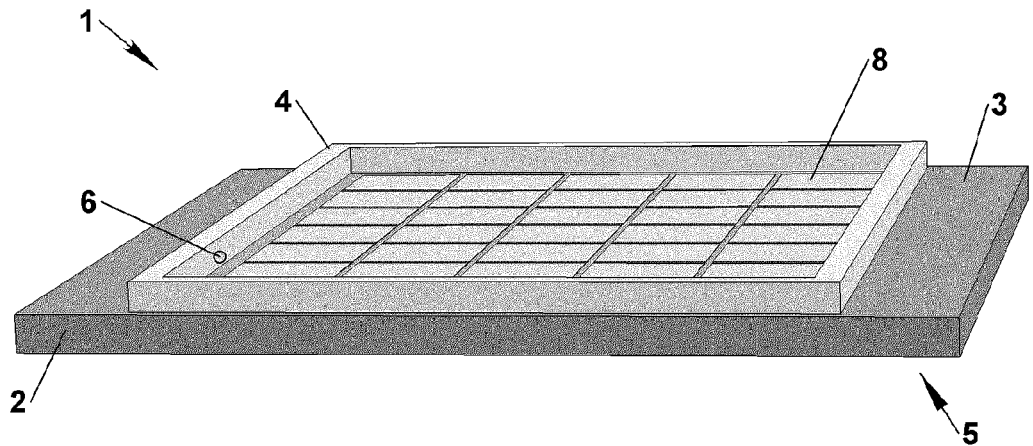
Prior Art Fig. 1A
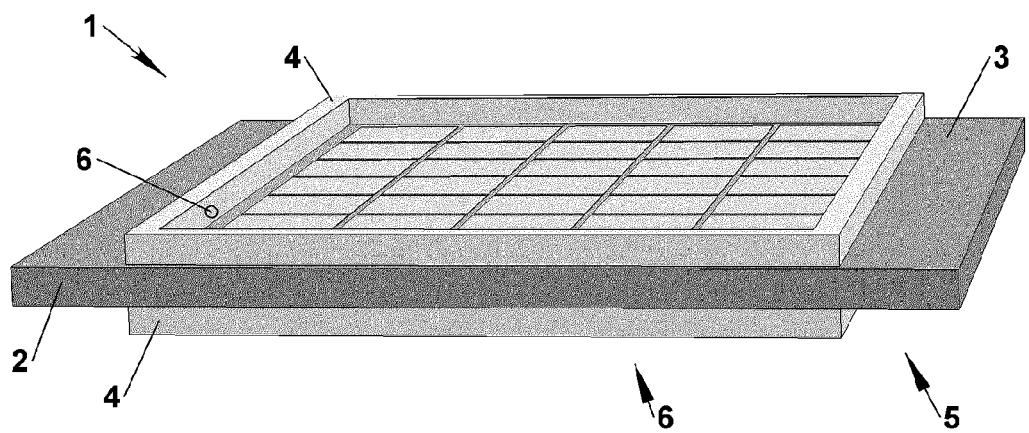
Prior Art Fig. 1B

Results With Pellicle
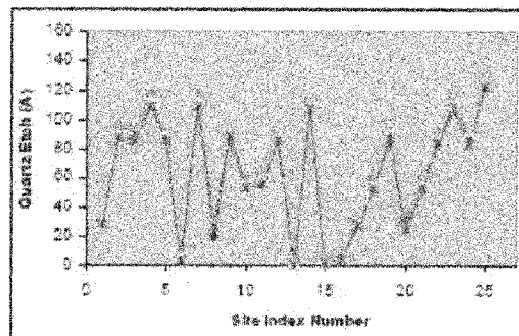
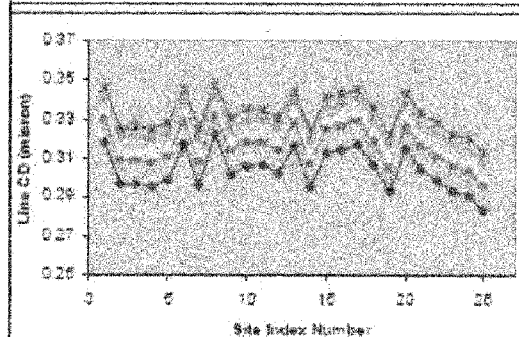
Results Without Pellicle
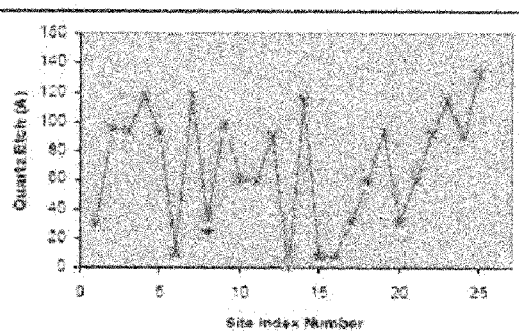
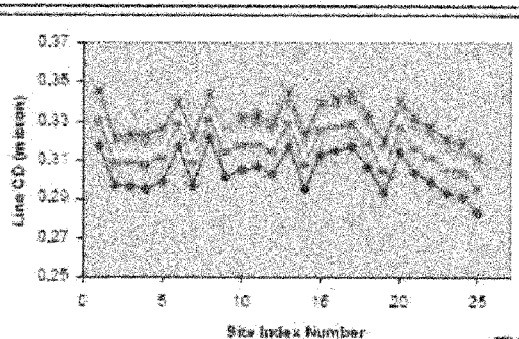
Fig. 6

SYSTEM AND METHOD FOR OPTICAL PHOTOMASK INSPECTION THROUGH PELLICLE

PRIORITY CLAIM

The present application claims priority to and from Provisional Patent Application titled "Photomask Measurement Through Pellicle" of the same inventors, Application No. 60/952,549, filed Jul. 27, 2007.

CROSS REFERENCE

The present invention cross references the US Patent Application of the same inventors titled "Automated Spatial Flipping Apparatus And System For Photomasks And Photomasks With Pellicles", application Ser. No. 12/050,387, filed Mar. 18, 2008, which is hereby incorporated by reference.

FIELD OF INVENTION

The present invention relates to systems and methods for photomask measurements through a pellicle on a measured photomask. In particular, the present invention relates to systems and methods for photomask measurements through a pellicle on a measured photomask by applying a previously determined pellicle correction factor.

BACKGROUND OF INVENTION

Referring to Prior Art FIGS. 1A, 1B, suppliers of photomasks 1 commonly apply a thin pellicle 6 over the mask 8 to protect it, after the final fabrication process has been completed. A pellicle 6 may also protect the bottom side 5 of the photomask 1. Such pellicles 6 may stay on the photomask 1 during its operational use to avoid dust particles that may otherwise contaminate the top layer of the mask 8. Spacing between the thin pellicle 6 and the top layer and/or the bottom 5 of the mask 8 as well as sealing is provided by a surrounding frame(s) 4. The spacing provides on one hand for sufficient clearance such that the thin pellicle 6 does not come into contact with the top layer irrespective eventual sagging of the pellicle 6. This may be particularly an issue with thin pellicles 6 commonly made of organic plastic material with thickness of about less than 10 micron, which are commonly employed with photomasks 1 operated during semiconductor fabrication in conjunction with light sources in the visual spectrum. Such thin pellicles 6 are highly homogeneous and introduce little and type consistent optical distortion. On the other hand, the spacing keeps dust articles that eventually deposit on top of the pellicle sufficiently far above the focal plane at the top layer such that beam distorting effects of eventual dust particles are kept to a minimum.

At the time of this invention and to the inventors knowledge, another form of pellicles 6 are emerging in conjunction with semiconductor fabrication techniques that employ ever shorter wave lengths in the ultraviolet light spectrum. Since organic plastic materials have significantly limited translucency for ultraviolet light and degrade relatively fast in such light, inorganic materials may increasingly need to be used for the pellicle 6. Such materials are commonly very brittle and are made with thickness of 100 microns up to about to 200 microns. With such thickness, the pellicle 6 may introduce optical distortions such as spherical aberrations to the light propagating through. Moreover and due to fabrication cost limitations, the inorganic pellicle 6 may be of limited optical quality with fabrication inconsistencies across its surface area that may introduce localized distortion characteristics. Another potential source of pellicle related optical distortions of the measurement is a well known localized thinning and thinning transitions of organic thin pellicles 6 exposed to radiation near 190 nm and below.

The photomask 1 needs to be inspected preferably through the pellicle 6, once fabrication is finished and prior to the operational use of it. Common photomask inspection devices have the optics very close to the photomask making unimpeded photomask inspection through the pellicle 6 difficult if not impossible to accomplish. In particular, thin film pellicles 6 may bulge in case of a thermal rise of the sealed volume. Hence, there exists a need for a photomask inspection device and method that provides for optical inspection of the photomask 1 with sufficient clearance to the pellicle. The present invention addresses this need.

Because of the emerging thick pellicles 6 for UV photomasks 1 that are visually hard to discern from thin pellicles 6, there exists a need for automatically identifying thin and thick pellicles 6 as well as type of thin and thick pellicles 6. The present invention addresses also this need. Further more and in cases of identified thick pellicles 6, there exists a need for identifying pellicle 6 in homogeneities and automated mapping of eventual localized optical distortion properties of the thick pellicle 6. The present invention addresses also this need.

During photomask inspection, a report of a number of well known properties of the photomask 1 itself is generated to document the quality of the fabricated photomask 1. In cases of thin and thick pellicles 6 used in the near and full UV spectrum, there exists also a need for documenting mapped local optical distortion properties of the pellicle 6, which may be also attributed to well known localized pellicle 6 thinning in cases of organic thin pellicle materials. The present invention addresses also this need.

SUMMARY

A system for photomask inspection through a pellicle on top and eventually on bottom of the photomask includes an optical n&k analyzer commercially available from n&k Technology™, a pellicle correction factor lookup table and a computing subsystem for computationally accessing the pellicle correction factor lookup table such that operational photomask measurements through the pellicle(s) may be computationally corrected for pellicle related optical distortions. In the pellicle correction factor lookup table may be stored pellicle correction factors that are computed from a first baseline measurement of a reference photomask without pellicle and from a second baseline measurement of the reference photomask with a reference type pellicle on the reference photomask. Pellicle correction factors may be pellicle type specific determined and may be provided to the system via well known data storage media or generated by the system itself. In the latter case, the first and second baseline measurements may be part of a baseline sampling procedure that is performed by the system. A logical routine computes the pellicle correction factor(s) by comparing the first and second baseline measurements eventually for each reference type pellicle and stores the computed pellicle correction factor(s) in the pellicle correction factor lookup table. During operational measurement of a generic photomask with a generic pellicle, a type matching pellicle correction factor may be applied to the raw measurement data such that measurement distorting effects of the generic pellicle are substantially cancelled out.

BRIEF DESCRIPTION OF THE FIGURES

Prior Art FIGS. 1A, 1B are simplified perspective views of prior art photomasks with pellicle and pellicle frame on one side and on both sides.

FIG. 6 are representative report graph generics of inspection results obtained of a generic photomask with thin pellicle on the left side and the same generic photomask without thin pellicle on the right side.

DETAILED DESCRIPTION OF THE INVENTION

Figure 2A:
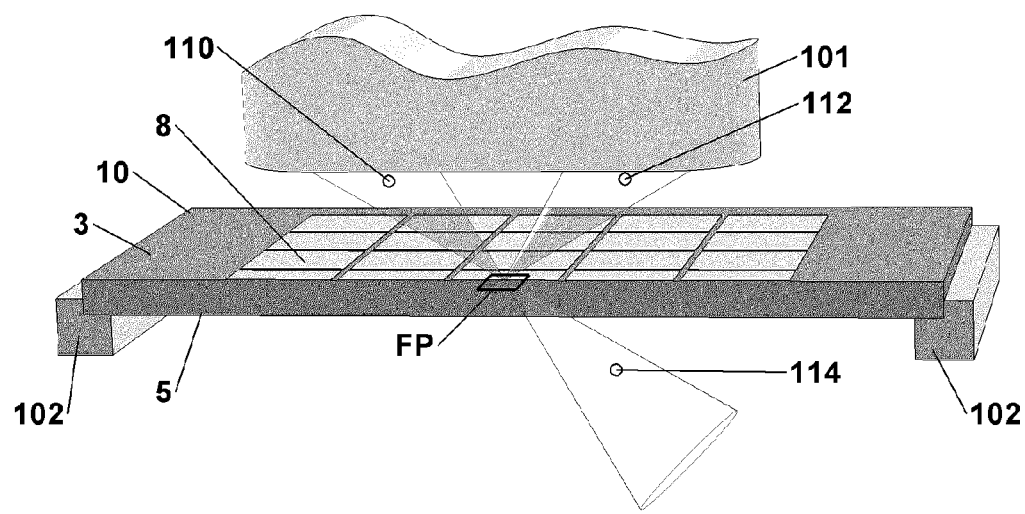
FIG. 2A, 2B are simplified perspective views of first baseline measurements on top and bottom sides of a reference photomask.

A photomask 1 with pellicle 6 as depicted in Prior Art FIGS. 1A, 1B may include a well known photomask that may have dimensions with 6 by 6 by ¼ inches. A thin pellicle 6 or thick pellicle 6 may extend across a pellicle frame 4 that attaches to the photomask 1. A representative frame that is 149 by 115 mm wide may have a conventional pellicle 6 height of about 5 mm. A pellicle 6 is typically located only on the top side 3, but eventually additionally or alternately on the bottom side 5 as well. The scope of the invention is not limited to a particular size of photomask 1 as may be well appreciated by anyone skilled in the art.

Figure 4:
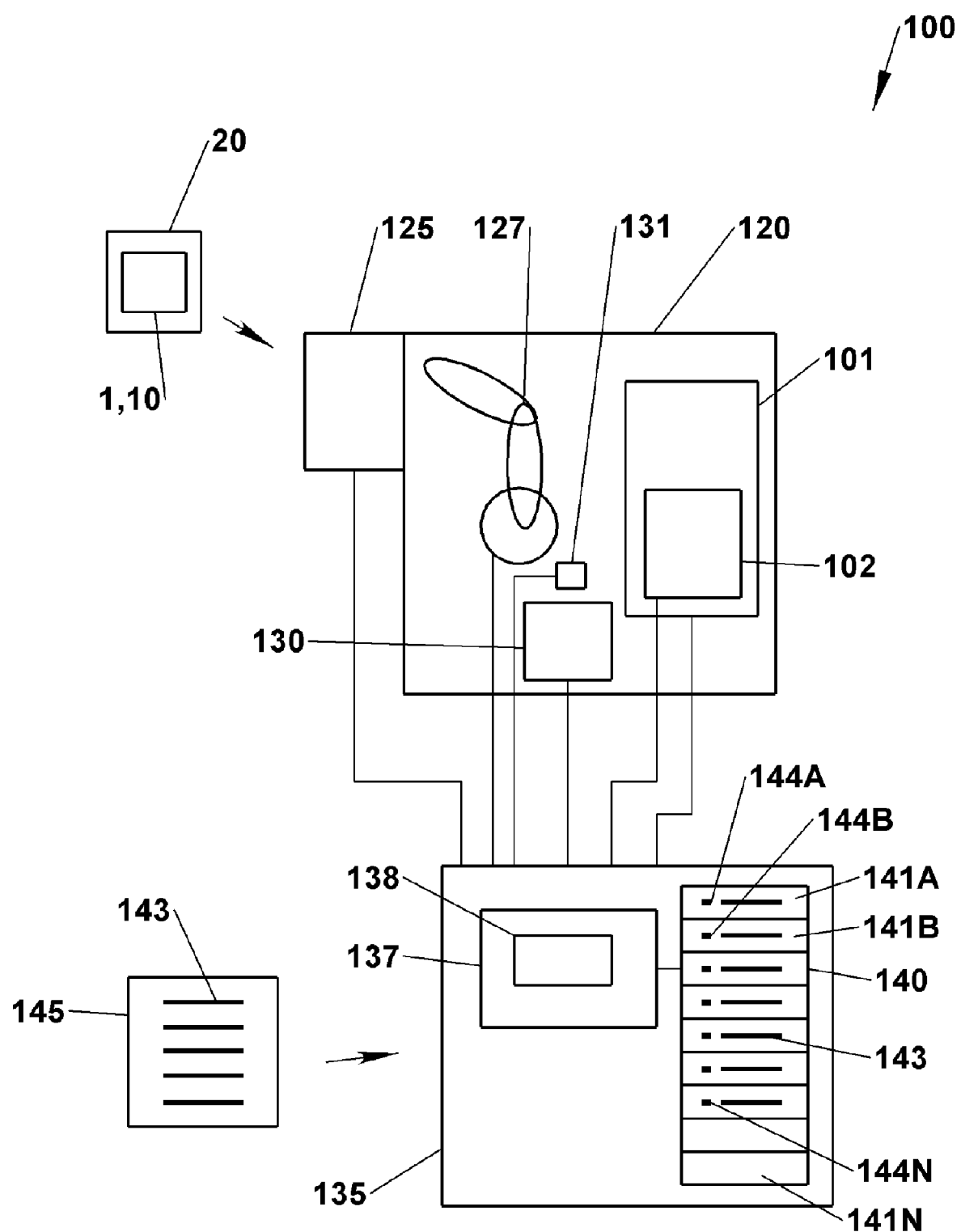
FIG. 4 is a schematic top view of a representative automated mask measurement system of the present invention.
Figure 5:
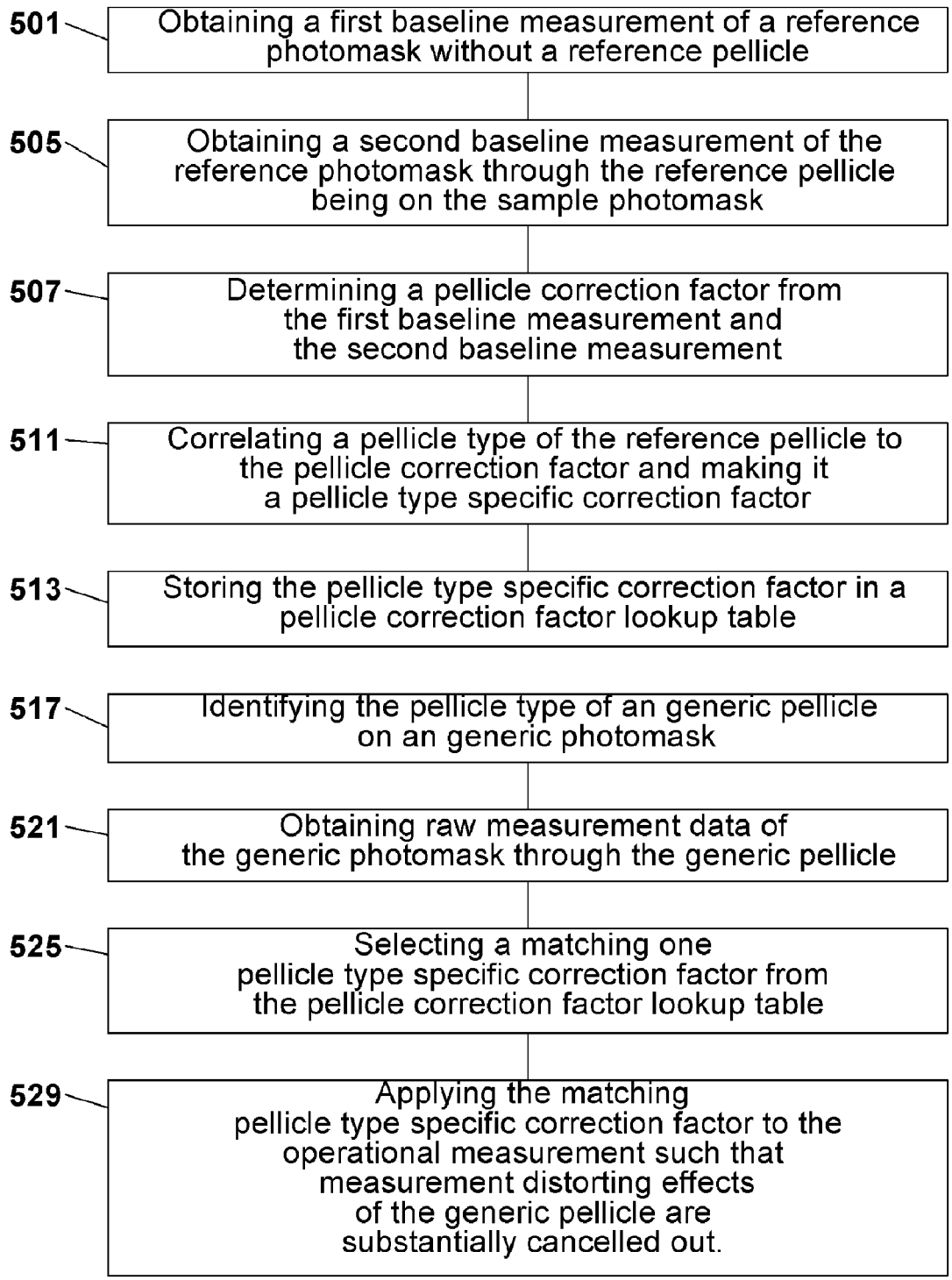
FIG. 5 is a block diagram of the method steps of the present invention.

As depicted in FIG. 4 and described in more detail in the cross referenced patent application, an automated photomask measurement system 100 may be employed that includes a well known transmittance and/or reflectance analyzer 101 such as well known n&k analyzers produced by n&k Technology™. Part of the n&k analyzer 101 is a well known generic holder 102, a photomask flipper/rotator 130, a mask robot 127, a photomask imaging system 131, and an SMIF loadport 125, all preferably combined on a mini environment frame 120 and controlled by a computing subsystem 135. Part of the system 100 is also a pellicle correction factor lookup table 140 that may be computationally accessible by the computing subsystem 135 in a well known fashion such that reflectance R and/or transmittance T measurements made with the analyzer 101 may be computationally corrected for pellicle 6 related optical distortions as described in more detail in the below.

Stored in the lookup table 140 and/or supplied to the system 100 via a well known data storage medium 145 in a lookup table 140 store able fashion may be one or more pellicle correction factors 143. The pellicle correction factors 143 are preferable pellicle type specific and may be provided to the system via the data storage medium 145 or generated by the system 100 itself. In the latter case, the first and second baseline measurements may be part of a baseline sampling procedure that may be performed by the system 100 and controlled by a logical routine 137. The logical routine 137 may automatically control the system 100 to examine reference photomask(s) 10 from the SMIF loadport 125 and to compute the pellicle correction factor(s) 143 by comparing a first baseline measurement of a reference photomask 10 without a reference pellicle 6 and a second baseline measurement of at least a reference pellicle 6 alone with the focal plane FP being in a spacing substantially equal the frame 4 height. The reference photomask 10 may be with or without mask layer 8 as may be clear to anyone skilled in the art. Nevertheless, the second baseline measurement may be preferably made of the reference photomask 10 and through the reference pellicle 6 being on the reference photomask 10 as shown in the FIGS. 2A-3B. The computed pellicle correction factor(s) 143 may then be stored in the pellicle correction factor lookup table 140 or the data storage medium 145 for later use. The data storage medium 145 may also be part of the system 100 without a lookup table 140, which may be the case for example of a single pellicle correction factor 143 being factory determined and shipped together with the system 100 to user utilizing a single type pellicle 6.

A number of arbitrarily oriented reference photomasks 10 and/or to be tested generic photomasks 1 may be stacked in a well known photomask SMIF Pod 20 and loaded by a user onto the SMIF loadport 125. From there, the mask robot 127 automatically takes one photomask 1/10 at a time and loads it on the photomask flipper/rotator 130 where the photomask 1/10 is rotated around a horizontal and vertical axis into a desired measurement orientation before it is again taken by the mask robot 127 and automatically transferred onto the generic holder 102 of the analyzer 101. After inspecting and analyzing the photomask 1/10, the mask robot transfers the photomask 1/10 from the generic holder 102 back to SMIF loadport 125. For more detail it is referred to the cross referenced patent application.

During operational measurement of a generic photomask 1 with a generic pellicle 6, the pellicle correction factor 143 may be applied preferably in a pellicle type specific fashion to the raw measurement data such that measurement distorting effects of the generic pellicle 6 are substantially cancelled out. First and second baseline measurements may be well known reflectance R and/or transmittance T measurements. In the preferred case of employed pellicle type specific correction factors 143, the pellicle type specific correction factors 143 may include a pellicle type identifier 144A-N and/or the pellicle correction factor lookup table 140 may feature pellicle type marked banks 141A-N as may be well appreciated by anyone skilled in the art. In the pellicle type marked banks 141A-N may a corresponding one pellicle type specific correction factor 143 be stored.

Referring to FIG. 2A, a particular feature of the n&k analyzer 101 is an extended clearance height between its optical head and the well known focal plane FP within which the emitted light beam 110 is focused. The extended clearance may be more than the conventional pellicle 6 height. The focal plane FP of the photomask analyzer 101 may consequently be moved onto the mask 8 top layer without the optical head colliding with the pellicle 6 or pellicle frame 4. Moreover, the optical head may be kept in a clearance above the pellicle 6 such that sufficient clearance is provided above a thin pellicle 6 that eventually bulges due to internal pressure rise in the sealed volume between the pellicle 6, the pellicle frame 4 and a reference photomask 10 or a generic photomask 1. In addition, the n&k analyzer 101 features a vertical travel range at least equal to the conventional pellicle 6 height for moving the focal plane FP on the pellicle 6 itself. In that way, identification of the pellicle 6 via the optical instrumentation of the photomask analyzer 101 may be accomplished as explained in more detail below under the second embodiment of the invention.

Referring to FIGS. 2A-3B and 5, a first embodiment of the invention is preferably employed in conjunction with highly type homogeneous pellicles 6 such as thin pellicles 6. Type homogenous in context with the present invention means that by examining a defined number of reference pellicles 6 of the same type, pellicle 6 information may be obtained for its optical distortion characteristics including reflectance and transmittance attenuation properties that may be applied in form of a pellicle type specific correction factor 143 for other pellicles 6 of that same type. As a result, by testing a representative number of reference pellicles 6 of a particular type such as a well known 193' pellicle or 248' pellicle for 193 nm wavelength light or 248 nm wavelength light respectively, pellicle type specific correction factors 143 for reflectance and transmittance may be calculated and applied to all consecutive generic photomask 1 measurements through a number of generic pellicle types the matching pellicle correction factors 143 of which have been previously determined.

Figure 2B:
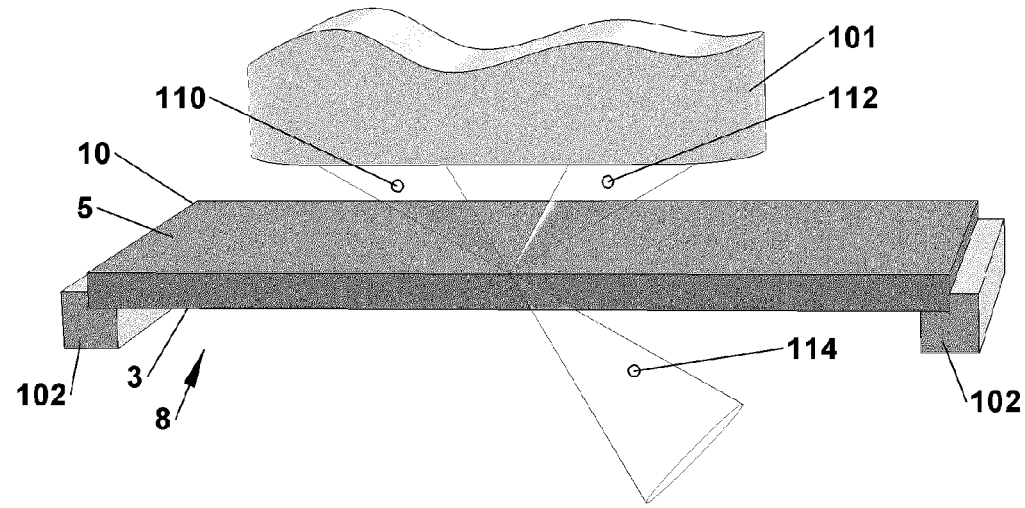

Initially and during a first baseline measurement of a reference photomask 10 without a reference pellicle 6 as shown in step 501 and FIGS. 2A, 2B an emitted beam 110 focused within the focal plane FP on the top 3 of the photomask 10 is partly reflected as reflected beam 112 and partly transmitted as transmitted beam 114 as is well known in the art. The first baseline measurement may be performed on top 3 of the reference photomask 10 as depicted in FIG. 2A and/or on the bottom 5 of the reference photomask 10 as depicted in FIG. 2B.

Figure 3A:
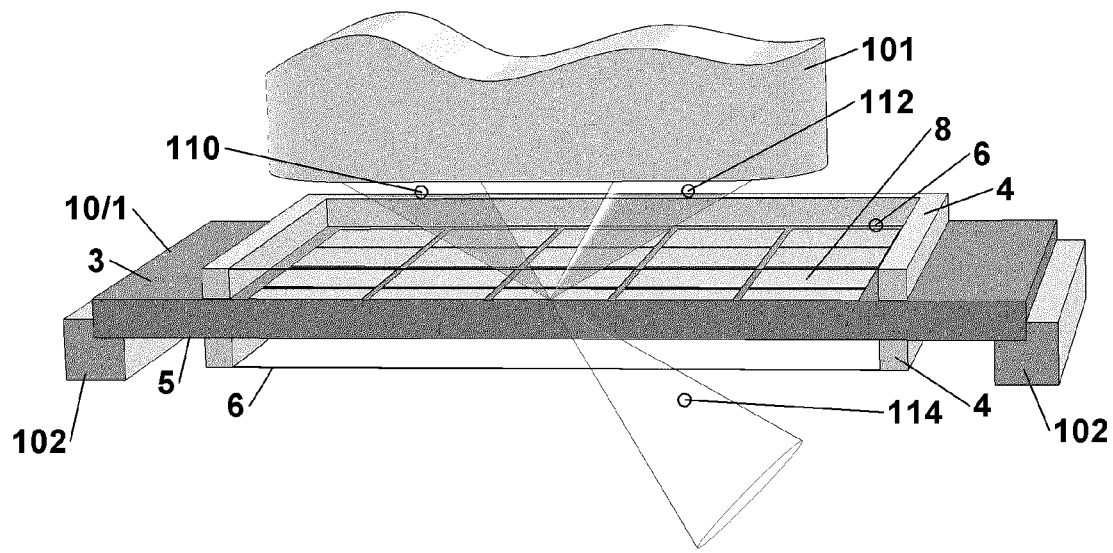
FIG. 3A, 3B are simplified perspective views of second baseline or operational measurements on top and bottom sides of a reference photomask with reference pellicle or a generic photomask with generic pellicle.
Figure 3B:
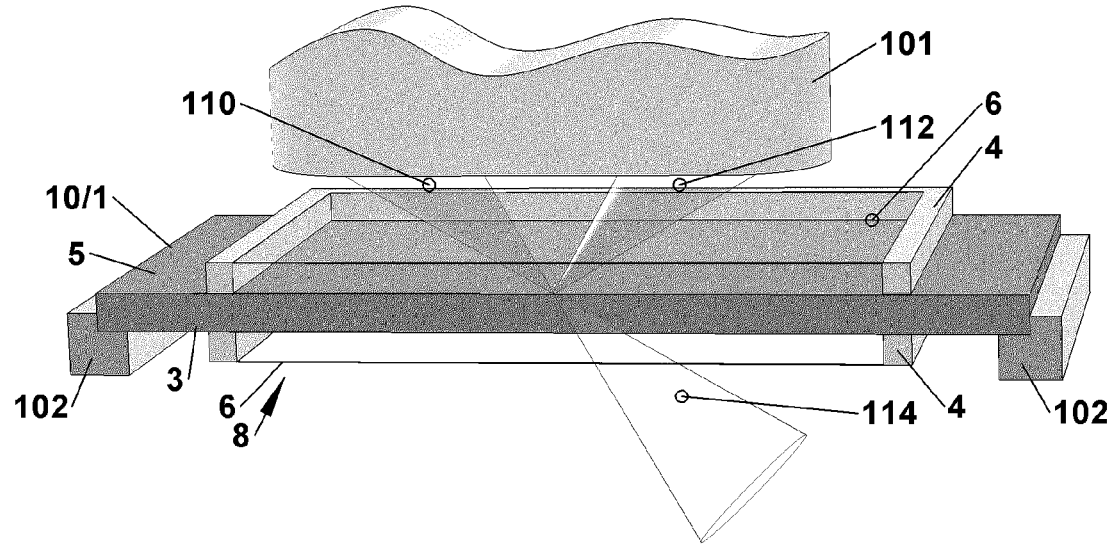

Referring to FIGS. 3A, 3B and during a following step 505 of testing a reference pellicle 6 of a particular type, a well known second baseline measurement of the reference photomask 10 is performed through the reference pellicle(s) 6 being on the reference photomask 10. Multiple first baseline measurements and/or second baseline measurements with different reference photomasks 10 and/or different reference pellicles 6 may reduce eventual measurement discrepancies. Thus, with well known statistical methods preferably computer assisted executed as a statistic routine 138, the pellicle type specific correction factors 143 may be determined with increased precision as shown in step 507. A pellicle type specific correction factor 143 may be for example determined for a 193 nm type pellicle 6 by dividing reflectance R and transmittance T results through air without pellicle 6 and through the pellicle 6 at all wavelengths within a predetermined light spectrum. Thereby, reflectance R at 633 nm of the reference photomask 10 through air during first baseline measurement may be 50%, whereas reflectance R at 633 nm of the reference photomask 10 through reference 193 nm type pellicle 6 during second baseline measurement may be 40%. The portion of the pellicle correction factor at 633 nm may consequently be 50 divided by 40 resulting in 1.25. The entire pellicle type specific correction factor 143 for a 193 nm type pellicle 6 may contain an array of reflectance R and/or transmittance T attenuation for all wavelengths within the predetermined spectrum similar to that described for 633 nm. As may be clear to anyone skilled in the art, pellicle type specific correction factors 143 hence preferably represent an R and/or T irradiation attenuation signature of a particular type pellicle 6 across the predetermined irradiation spectrum and may be calculated also in other ways than by division of first and second baseline measurements.

A number of different pellicle type specific correction factors 143 for a number of pellicle types may be generated by repeating steps 501, 505, 507, 511 and may be stored in the pellicle correction factor lookup table 140. The pellicle correction factor lookup table 140 may be stored in memory of the computation subsystem 135 that is part of the system 100.

The computation subsystem 135 may also automatically and software controlled execute the steps of the invention. Nevertheless, pellicle correction factor(s) 143 may be supplied to the system 100 on any well known data storage medium 145 including but not limited to well known hard disks, CD, DVD, SD card, self extracting computer executable file, compressed computationally readable data files and encrypted computationally readable data files as are well known in the art. The pellicle correction factor 143 may be preferably pellicle type specific and stored on the data storage medium 145 in a fashion such that the pellicle correction factor 143 is pellicle type specific interpretable by accessing the data storage medium 145 as may be well appreciated by anyone skilled in the art.

Once pellicle type specific correction factors 143 preferably for reflectance and transmittance are determined and stored in a pellicle correction factor lookup table 140 or made otherwise available in a well known fashion to the system 100 as in step 513, any generic photomask 1 featuring an generic pellicle 6 of that particular type may be measured. During a following step 517, the pellicle type of the generic pellicle 6 on the generic photomask 1 is identified, by use of an automated imaging 131 and image interpretation system as described in the cross referenced application. Generic pellicle 6 identification may also be accomplished in any other well known automated or manual fashion and/or as described under the second embodiment of the invention below.

Once the type of the generic pellicle 6 is identified, a matching pellicle type specific correction factor 143 may be selected from the pellicle correction factor lookup table 140 as in step 525. As shown in step 529, the matching pellicle type specific correction factor 143 may be applied to the raw measurement data of the generic photomask 1 through the generic pellicle 6 of step 521 and FIGS. 3A, 3B. The raw measurement data may be obtained via the top 3 and/or the bottom 5 of the generic photomask 1 as depicted in FIGS. 3A and 3B.

The pellicle type specific correction factor 143 may be applied to the raw measured reflectance R and transmittance T data to eliminate the distorting effects of the pellicle 6. Finally, the new corrected R and T data with the applied pellicle type specific correction factor 143 may be analyzed to derive well known information about the generic photomask 1 itself. As shown in FIG. 6, representative measurement of a generic photomask 1 with generic pellicle 6 and application of the invention renders measurement results that are highly similar to measurement results obtained from the same generic photomask 1 measured without generic pellicle 6.

In a second embodiment of the invention, identification of the pellicle type may be obtained by moving the focal plane FP onto the pellicle 6 and measuring direct optical properties of the pellicle 6 rather than indirectly determining its distorting properties as described in the first embodiment. In that way and during reference pellicle testing, a type differentiable optical signature of the pellicle type may be determined and stored together with the type related correction factors 143 in the lookup table 140. During operational photomask inspection and without prior knowledge of the pellicle type, the pellicle type may be identified by moving the focus plane FP onto the pellicle 6 surface. Once the optical signature is determined it may be compared to the pellicle signatures in the lookup table 140. Upon identification of a matching optical pellicle signature, the corresponding correction factors are consecutively extracted from the lookup table and applied. Pellicle type identification may include thin and/or thick pellicles. This pellicle type identification may be employed in step 517.

A third embodiment may be employed in the case of pellicles 6 with higher risk of distortion inhomogeneities such as thick pellicles 6 or thin pellicles 6 of organic material that are operationally exposed to near UV radiation and that bear the well known operational risk of localized pellicle thinning. In such cases, the optical type signature described in the second embodiment may be repeatedly performed in an exploratory fashion and/or in conjunction with thinning risk map that may be correlated to the photomask's 1 layout. During such exploratory fashion and upon eventual initial pellicle type identification, a predetermined coarse location matrix on the pellicle is inspected by use of the analyzer's 101 photomask inspection instrumentation.

In a first case in which the optical measurement discrepancies of the pellicle 6 at all matrix locations are within a predetermined low threshold, further measurement is aborted and a single set of correction factors 143 is applied for the entire pellicle 6 area. In a second case in which the location matrix measurement discrepancies between adjacent location measurements fall within a predetermined high threshold, individual correction factors are applied for each area surrounding that matrix location. In a third case in which the adjacent location matrix measurement discrepancies exceed the predetermined high threshold, the location matrix spacing is reduced and the location number increased. The optical pellicle inspection as well as discrepancy/high threshold comparison is then repeated with the more dense modified location matrix. In that fashion, the location matrix may be repeatedly adjusted and optical location measurement repeated on the pellicle 6 until adjacent measurement discrepancies remain within the predetermined high threshold. The individual correction factors are obtained as described in the first embodiment. In that fashion, inexpensive thick pellicles 6 of relatively poor optical quality may be employed while obtaining undistorted measurements across the entire photomask 1 irrespective eventual distortion fluctuation across the pellicle 6 area. The mapped localized optical distortion properties of the pellicle that are obtained in the fourth embodiment may also be documented together with the photomask 1 inspection report.

Also, the mapped optical distortion properties of the pellicle 6 of the tested photomask 1/10 may be stored as computer readable data on the data storage medium 145 for further optically corrective action during semiconductor fabrication steps including the tested generic photomask 1/10 with its generic pellicle 6.

Accordingly, the scope of the present invention described in Figures and Specification above is set forth by the following claims and their legal equivalent:

What is claimed is:

1. A system for optical photomask inspect through pellicle comprising:
   a. an optical analyzer for at least one of a reflectance and a transmittance measurement of a photomask and through a pellicle being on said photomask;
   b. a pellicle correction factor lookup table;
   c. a pellicle type specific correction factor that is at least one of stored and store able in said pellicle correction factor lookup table, said pellicle correction factor being computed from a first baseline measurement of a reference photomask without a reference pellicle and from a second baseline measurement of at least said reference pellicle;
   c. a computing subsystem for computationally accessing said pellicle correction factor lookup table such that at least one of said reflectance and transmittance measurement is computationally correctable for pellicle related optical distortions; and
   wherein said pellicle correction factor lookup table comprises a pellicle type marked bank, and wherein said pellicle type specific correction factor is stored in said pellicle type marked bank.

2. The system of claim 1, wherein said first baseline measurement and said second baseline measurement include a reflectance measurement.

3. The system of claim 1, wherein said first baseline measurement and said second baseline measurement include a transmittance measurement.

4. The system of claim 1, wherein said pellicle type specific correction factor includes a pellicle type identifier.

5. The system of claim 1, wherein said pellicle correction factor is an irradiation attenuation signature across a predetermined irradiation spectrum.

6. The system of claim 1, wherein said computing subsystem further comprises a logical routine for automatically performing a baseline sampling and for computing a pellicle correction factor from said baseline sampling and for storing said computed pellicle correction factor in said pellicle correction factor lookup table.

7. The system of claim 6, wherein said optical analyzer comprises a configuration for said baseline sampling.

8. The system of claim 6, wherein said baseline sampling comprises a first baseline measurement of a known reference photomask without a reference pellicle and from a second baseline measurement of at least said reference pellicle.

9. The system of claim 8, wherein said first baseline measurement and said second baseline measurement include a reflectance measurement.

10. The system of claim 8, wherein said first baseline measurement and said second baseline measurement include a transmittance measurement.

11. The system of claim 8, wherein said baseline sampling comprises multiple of said first baseline measurement and said second baseline measurement, and wherein said logical routine further comprises a statistic routine for computationally determining said pellicle correction factor from said multiple first and second baseline measurements.

12. The system of claim 1, wherein said optical analyzer is an n&k analyzer.

\* \* \* \* \*